(12) United States Patent
Mapleson et al.

(10) Patent No.: US 7,226,775 B2
(45) Date of Patent: Jun. 5, 2007

(54) METHOD OF REMOVING ENDOTOXIN FROM VACCINES

(75) Inventors: Bridget Kathleen Mapleson, Liverpool (GB); Philip Sizer, Helsby (GB)

(73) Assignee: Medeva Europe Limited, London (GB)

(*) Notice: Subject to any disclaimer, the term of this patent is extended or adjusted under 35 U.S.C. 154(b) by 0 days.

(21) Appl. No.: 09/803,778

(22) Filed: Mar. 12, 2001

(65) Prior Publication Data

US 2001/0053366 A1    Dec. 20, 2001

Related U.S. Application Data

(63) Continuation of application No. 09/463,762, filed as application No. PCT/GB98/02314 on Jul. 31, 1998, now abandoned.

(30) Foreign Application Priority Data

Jul. 31, 1997    (GB) ................... 9716242.4

(51) Int. Cl.
*C12N 7/02* (2006.01)
(52) U.S. Cl. ................ 435/239; 424/204.1; 424/209.1; 424/210.1
(58) Field of Classification Search ............. 424/204.1, 424/209.1, 210.1; 435/239
See application file for complete search history.

(56) References Cited

U.S. PATENT DOCUMENTS 4,315,919 A * 2/1982 Shanbrom

FOREIGN PATENT DOCUMENTS

EP    0 083 999 A1    7/1983
WO    WO 95/21179    8/1995

OTHER PUBLICATIONS

Petsch, D. et al., "Membrane Adsorbers for Selective Removal of Bacterial Endotoxin," *J. Chrom. B.*, 693:79-91 (1997).
Schindler, R. and Dinarello, C.A., "A method for removing interleukin-1 and tumor necrosis factor-inducing substances from bacterial cultures by ultrafiltration with polysulfone," *J. Immun. Methods*, 116:159-65 (1989).
Dawson, M. et al., "Microbes, Endotoxins and Water," *Pharm. Engineering*, 8:20-23 (1988).
Sweadner, K.J. et al., "Filtration Removal of Endotoxin (Pyrogens) in Solution in Different States of Aggregation," *Applied and Environmental Microbiology*, 34:382-85 (1977).
Nagy, L.K., "The Effect of Deoxycholate on Cholera Vaccine," *Progr. Immun. Standard*, 5:341-47 (1972).
McIntire, F. et al., "Studies on a Lipopolysaccharide from *Escherichia coli*, Heterogeneity and Mechanism of Reversible Inactivation of Sodium Deoxycholate," *Biochemistry*, 8:4063-66 (1969).

* cited by examiner

*Primary Examiner*—Robert A. Zeman
(74) *Attorney, Agent, or Firm*—Heslin Rothenberg Farley & Mesiti P.C.; Kathy Smith Dias; Charles E. Bell (57) ABSTRACT

A method of removing bacterial endotoxin from a pharmaceutical process solution is disclosed. In one embodiment, the method comprises treating the solution with a surfactant effective to dissociate the endotoxin from a pharmaceutical drug or vaccine substance in the solution, and then filtering the solution through a molecular cut-off filter having a pore size effective to retain the pharmaceutical drug or vaccine substance but allow the dissociated bacterial endotoxin to pass therethrough.

12 Claims, 9 Drawing Sheets

SEC Profile (above: A = 280nm), below: A = 320nm

SEC Profile (above: A = 280nm), below: A = 320nm

METHOD OF REMOVING ENDOTOXIN FROM VACCINES

PRIOR FOREIGN APPLICATIONS

This application is a continuation of U.S. patent application Ser. No. 09/463,762, filed Apr. 27, 2000 now abandoned as a 35 USC §371 filing of International Patent Application Number PCT/GB98/02314, filed Jul. 31, 1998 and claims priority from GB Patent Application Number 9716242.4, filed Jul. 31, 1997. The entire disclosures of the earlier applications are incorporated herein by reference.

FIELD OF THE INVENTION

This invention relates to a method of removing bacterial endotoxins from pharmaceutical compositions, e.g. vaccine compositions.

BACKGROUND OF THE INVENTION

Endotoxins are lipopolysaccharides which are typically derived from the cell walls of bacteria, and in particular Gram negative bacteria. Contamination with endotoxin is a common problem in the pharmaceutical industry, particularly in non-sterile production processes.

Vaccines, for example viral vaccines, can be produced by inoculating a suitable viral substrate with a virus, incubating the substrate to allow viral replication and then harvesting the virus from the substrate. The virus is then inactivated using a suitable inactivating agent and the viral solution is further processed and purified to give the vaccine.

In one method of producing vaccines, and in particular viral vaccines such as influenza vaccine, eggs are used as the substrate for the virus. Thus the eggs are inoculated with seed virus, incubated to allow viral replication, and the allantoic fluid containing the virus harvested from the eggs. The allantoic fluid is then subjected to a sequence of purification steps to give a purified viral fraction which may then be lysed with a detergent such as Triton to disrupt the virus and release the desired viral antigens. The viral antigens are further purified and optionally blended, where desired, with other antigens to give a multivalent vaccine composition. Preparation of the vaccines is typically conducted in sterile rooms, and preservatives such as thiomersal are added at various stages during the process to minimise or prevent bacterial growth.

When eggs are used as the viral substrate, although they go through a cleaning process prior to inoculation to reduce the bioburden, the cleaning process does not guarantee complete removal of microorganisms. Moreover, it is possible that the eggs may not be pathogen free and may contain bacteria. Consequently, during the period of viral growth in the eggs, any contaminating bacteria will also multiply. Although the bacteria may be killed by preservative, the endotoxin-containing bacterial cell walls remain. During the disruption of the viral particles with detergent, the bacterial cell walls are also ruptured leading to release of endotoxin which may copurify into the final vaccine composition. If high levels of bacterial endotoxin are detected in the vaccine, current practice is to discard the contaminated vaccine rather than attempt to remove the endotoxin. As a consequence, there can be significant and expensive wastage during vaccine production as a result of endotoxin contamination.

Endotoxin contamination represents a particular problem in the manufacture of influenza vaccines. The primary constituents of influenza vaccines are the haemagglutinin (HA) surface antigens, along with smaller amounts of neuraminidase surface antigens (NA). Both the HA and NA can form characteristic rosette structures, either alone or as mixed rosettes containing both types of antigens. This behaviour is typical of membrane proteins where the hydrophobic stalks which traverse the membrane are forced to self-associate to produce a stable hydrophobic microenvironment.

The haemagglutinins generally exist in the form of trimers whilst the neuraminidase antigens tend to exist in tetrameric forms. Once formed, the rosettes are very stable and, for example, are not easily disrupted with detergents (Sian Renfrey PhD Thesis, University of Oxford 1994).

Bacterial endotoxins are lipopolysaccharides which possess a large hydrophilic polysaccharide chain, and a hydrophobic fatty acid-containing tail. Thus they have an amphiphilic structure. When in an aqueous environment, there will be a tendency for them to form aggregates.

It has been found that influenza surface antigens and endotoxin are difficult to separate from one another, and it is believed that this may be due to the fact that both influenza surface antigens, such as HA, and endotoxin have an amphiphilic structure and may become strongly associated under aqueous conditions. It also appears that endotoxin is incorporated into the HA/NA rosettes.

Any method of removing endotoxin from vaccine compositions must fulfil a number of criteria. Firstly, the method must not result in excessive loss of the product antigen. Secondly, it must be capable of removing relatively high concentrations of endotoxin (for example it should be capable of reducing the levels of endotoxin to less than 200 EU/ml, e.g. to less than 100 EU/ml). The method must not introduce potentially toxic chemicals into the product and any chemicals which are used must not adversely affect the antigens. Any such method must also be suitable for scaling up for use under production conditions. A method which works on only a small scale, but cannot be scaled up efficiently, is of no use in a manufacturing context. Finally, it is desirable that the method of removal of endotoxin should be capable of being carried out using existing process and production equipment.

A number of attempts have been made to remove endotoxin from vaccines but these have hitherto been generally unsuccessful.

Sucrose density gradient centrifugation is a technique which relies on the separation of substances on the basis of their specific molecular densities, assuming that there is no interaction between them. This technique has been applied by the present applicants to the problem of endotoxin removal from influenza antigen solutions; it was found that although 30% of the endotoxin eluted separately from the haemagglutinin on the sucrose density gradient, the remaining 70% remained associated with the surface antigen. Addition of detergent to the sucrose density gradients only improved endotoxin resolution from haemagglutinin by a relatively small extent.

It has been reported that triethylamine interacts with endotoxin causing an increase in endotoxin hydrophobicity and hence it was postulated that triethylamine may induce separation of the HA/NA/endotoxin complex believed to be formed. Triethylamine was therefore added to the sucrose density gradient, but this was unsuccessful in improving the resolution of endotoxin from haemagglutinins.

Non specific absorption of endotoxin onto activated charcoal, glass, anion exchange media (DEAE) and polystyrene have also been attempted but such attempts were not successful.

A number of affinity chromatography media are commercially available for the purpose of removing endotoxin from pharmaceuticals. The proprietary detoxifying media "Acticlean Etox, Prosep-Remtox and CUNO Zeta Plus ZA" were tried with varying degrees of success. Thus "Acticlean Etox" was successful in separating 99% of the endotoxin from the haemagglutinins in a small scale experiment, but the small scale separation could not be reproduced adequately and the method did not work effectively on a larger scale. "Prosep-Remtox" did not adsorb either endotoxin or haemagglutinin, whereas CUNO Zeta Plus ZA" adsorbed 100% endotoxin and 100% haemagglutinin.

Thus, there remains a pressing need for a method of removing endotoxin from pharmaceutical compositions, and in particular vaccine compositions.

SUMMARY OF THE INVENTION

It is an object of the present invention to provide a method of removing endotoxin which is effective on a manufacturing scale, does not leave toxic or objectionable chemical residues in the pharmaceutical product, is compatible with conventional process equipment and, particularly in the case of vaccine, does not result in the excessive loss or denaturing of antigen.

It has now been found that influenza surface antigens, such as HA and NA, and endotoxin can be separated by addition of a detergent and then filtering the resulting mixture through a molecular weight cut-off (MWCO) filter having a pore size such that the antigen remains in the filter retentate whilst the endotoxin passes through the filter with the filtrate. It is envisaged that this technique will also be applicable to other pharmaceutical products and in particular drugs and vaccines which contain polypeptide chains or have an amphiphilic structure.

Accordingly, the invention provides a method of removing bacterial endotoxin from a pharmaceutical process solution which method comprises treating the solution with a surfactant effective to dissociate the endotoxin from a pharmaceutical drug or vaccine substance in the solution, and then filtering the solution through a molecular weight cut-off filter having a pore size effective to retain the pharmaceutical drug or vaccine substance but allow the dissociated bacterial endotoxin to pass therethrough.

The term "pharmaceutical process solution" as used herein refers to any pharmaceutical drug substance-containing or vaccine antigen-containing solution that may be produced as part of the pharmaceutical manufacturing process, up to and including the final product. The pharmaceutical process solution may, for example, be a solution of partially purified vaccine antigens from which cell debris or unwanted materials from a microbial particle (e.g. a viral particle) or cell have been removed.

The pharmaceutical substance can be any pharmaceutical drug or vaccine substance which is susceptible or potentially susceptible to endotoxin contamination during its manufacturing process. For example, the substance can be a vaccine antigen or a therapeutic polypeptide product such as a peptide hormone, or a blood product. In particular, the therapeutic peptide product can be a recombinant peptide product. The terms "peptide" and "polypeptide" as used herein embraces substances which consist solely of peptides, as well as substances such as glycoproteins which comprise peptides in association with or bonded to other moieties such as saccharide groups.

The substance will typically be one which associates with the endotoxin, for example forming a complex. Non-peptide drugs which have amphiphilic structures, and which consequently may form complexes with endotoxins, may also benefit from the method of the present invention.

The surfactant can be a cationic, non-ionic, zwitterionic, amphoteric or anionic surfactant, provided that it is effective to dissociate the endotoxin from the antigen whilst not adversely affecting the properties of the antigen and in particular its ability to be retained on the MWCO filter. Preferably, however, it is an ionic surfactant and in particular an anionic surfactant.

Particular surfactants are anionic surfactants having a steroidal structure, and in particular the surfactants corresponding to or analogous to bile salt acids. Thus, for example, the surfactant can be a suitable salt of deoxycholate, cholate, glycocholate, taurodeoxycholate or taurocholate for example. Salts of deoxycholate (DOC) are presently preferred.

Other examples of anionic surfactants include long chain alkyl and alkylaryl sulphonates such as alkyl-benzene-sulphonates and dodecylsulphonate.

The concentration of surfactant will be one which is effective to dissociate the endotoxin from the antigen whilst not having an adverse effect on the antigen or its ability to be retained on the MWCO membrane. Preferably the concentration of the surfactant is at least equal to its critical micelle concentration (CMC), and more preferably is greater than its critical micelle concentration. It is presently most preferred to use concentrations of surfactant of one and a half to five times, for example two to four times, the critical micelle concentration.

The surfactant is most preferably one which can readily be removed from the product, for example by dialysis techniques.

The molecular weight cut-off (MWCO) filtration membrane is selected so as to have a molecular weight cut-off which enables retention on the membrane of the desired product antigens, but which allows the endotoxin and surfactant to pass through the membrane.

For example, with influenza antigens, a 100 kD MWCO membrane can be employed. This will retain the majority of the haemagglutinin antigens which typically exist in a trimeric form having a molecular weight of approximately 230 kD.

It is possible that the endotoxin forms micelles or aggregates with the surfactant and, in such circumstances, the surfactant should be such that the total molecular weight of any micelles formed with the endotoxin is less than the molecular weight cut-off of the filter membrane.

The membrane can be, for example, a regenerated cellulose acetate membrane, or a polysulphone membrane. A particular example of a membrane suitable or use in the method of the present invention is the 100 kD MWCO cellulose acetate Millipore membrane.

The method of the present invention has been found to be useful for separating bacterial endotoxin from the influenza viral surface antigens, but it is envisaged that the method will also find application with other viral, bacterial, protozoal and parasitic vaccine antigens, and in particular other haemagglutinin antigens, as well as other polypeptide substances and other drug substances in which endotoxin contamination is a problem.

The method of the invention will now be illustrated, but not limited, by reference to the following examples.

DETAILED DESCRIPTION OF THE PREFERRED EMBODIMENTS

Figure 1:
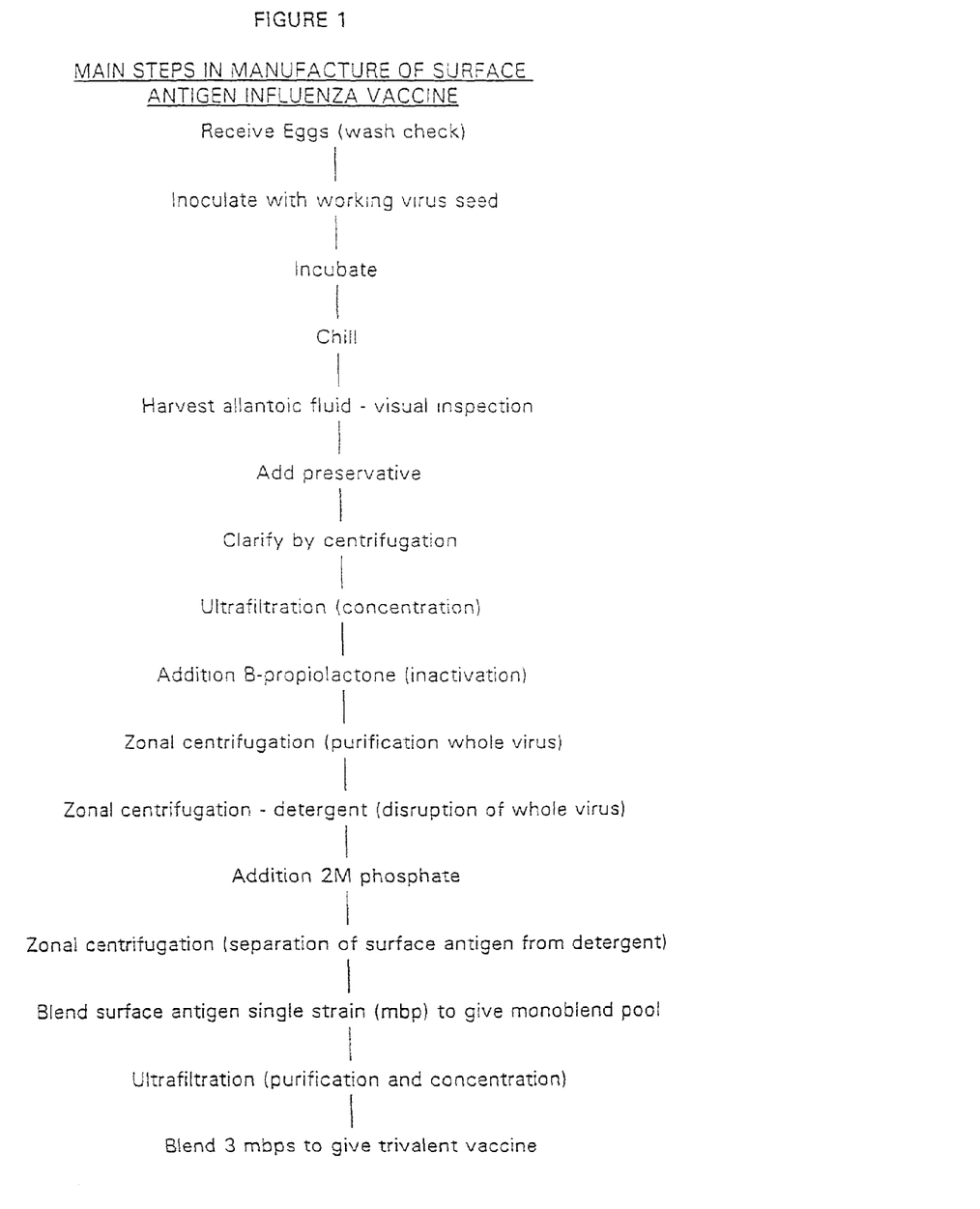
FIG. 1 illustrates schematically the main stages involved in the manufacture of a vaccine.

FIG. 1 illustrates schematically the typical sequence of steps involved in the manufacture of an influenza vaccine. Thus, chicken eggs are first washed to remove external contaminants, inoculated with working virus seed and then incubated to allow viral growth and multiplication to take place within the eggs. At the end of the viral incubation step, the eggs are chilled and the allantoic fluid containing the virus is harvested from the eggs.

After harvesting, a preservative (which may be thiomersal) is added. The resulting preserved solution is then centrifuged to clarify the solution and subjected to ultrafiltration to concentrate the viral components.

Following concentration, the solution is treated with a virus-inactivating agent which may be, for example, β-propiolactone, before the whole virus is purified by zonal centrifuge.

The purified viral fraction is then treated with a detergent such as Triton N101 to disrupt the viral particles and the resulting mixture is then subjected to zonal centrifugation to separate the denser viral core materials from the influenza surface antigens.

Following the addition of phosphate buffer, the surface antigen is then separated from the detergent by zonal centrifugation to give a single strain antigen solution. Batches of solution from separate production runs can then be pooled to give a "Monoblend Pool" (MBP) which can then be further purified and concentrated by ultrafiltration before blending with monoblend pools from other viral strains to give a multivalent vaccine.

During the foregoing process, the levels of endotoxin are usually measured at several points and, if the levels at a given point are higher than the predetermined limit, the batch is discarded, under the procedures in place before the present invention.

However, it has been found that the endotoxin can be removed by subjecting the Monovalent Blend Pool (MBP) to treatment with a suitable detergent to disrupt any bonding between the endotoxin and the purified surface antigens and then filtering the resulting mixture through a molecular weight cut off filter of a grade sufficient to allow endotoxin through but retain the purified surface antigen. Purified surface antigen substantially free of endotoxin can then be recovered from the filter retentate. The following experiments illustrate the effect of treatment with the anionic detergent sodium deoxycholate and subsequent MWCO filtration through a 100 kD cut off filter on endotoxin levels.

EXAMPLE 1

Small Scale Study

Small scale studies on the effects of 2% w/v (50 mM) and 0.2% w/v (5 mM) concentrations of sodium deoxycholate on removal of endotoxin by a 100 kD MWCO filter were carried out on a sample of A/Texas/36/91 batch 531 MBP containing approximately 10,000 EU/ml of the antigen. The antigen sample prepared in accordance with the method described above consisted essentially of haemagglutinin and neuraminidase purified surface antigens in 10 mM phosphate buffered saline at pH 7.2 containing 0.15M sodium chloride and 0.01% thiomersal.

Sodium deoxycholate (DOC) has a tendency to form gels at pH values lower than its pKa value. In order to prevent gel formation, the pH of the antigen sample was first adjusted to a value of pH 8 or greater prior to addition of the detergent. Thus, 2% w/v (0.14M) disodium phosphate was added to the MBP which was warmed to 37° C. taking care to ensure that the disodium phosphate was completely dissolved. The pH of the MBP was thereby raised from approximately pH 7.4 to a value of pH 8.1. The sodium ion concentration of the resulting solution was approximately 0.3M.

Figure 2:
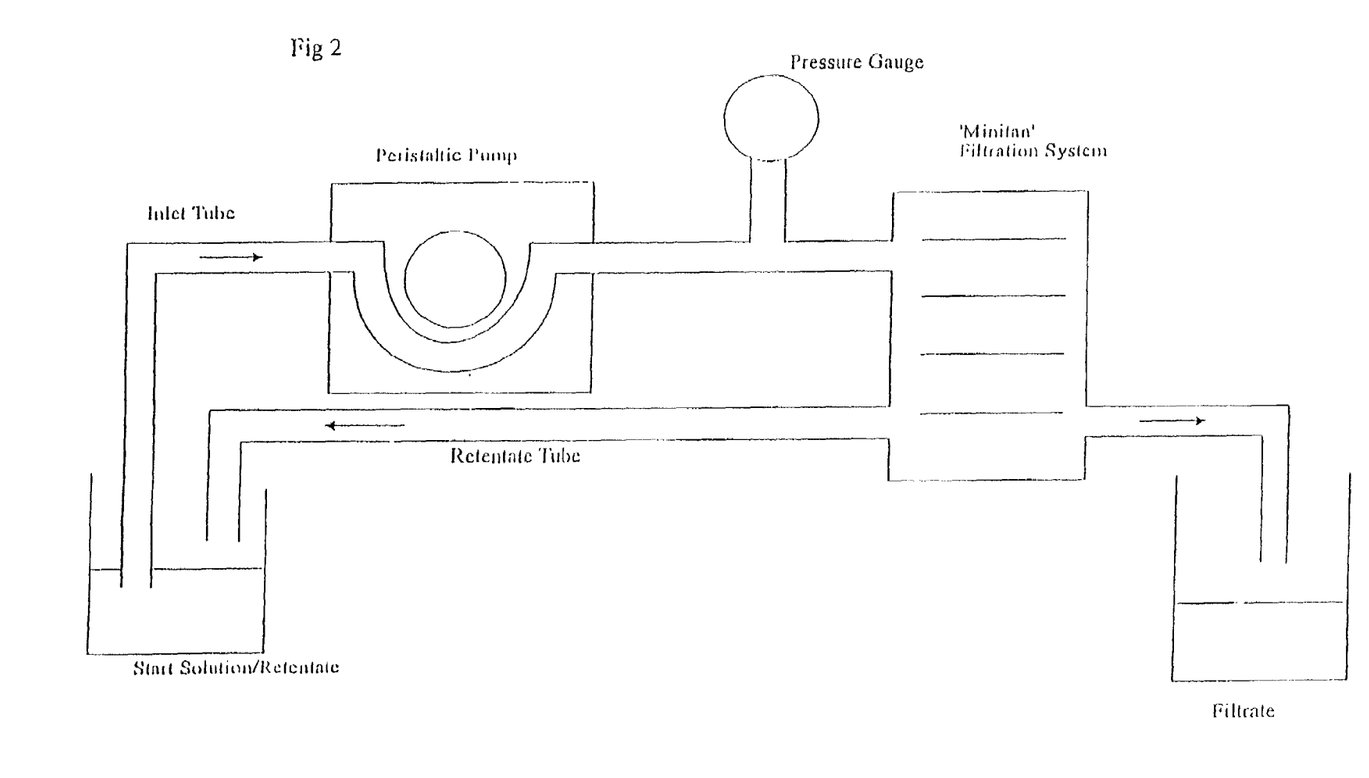
FIG. 2 is a schematic illustration of an MWCO diafiltration apparatus used in the method of the present invention.

Sodium deoxycholate was added to the MBP solution to give test solutions having final concentrations of 0.2% w/v (5 mM) and 2% w/v (50 mM) DOC, and the test solutions were incubated at 37° C. for approximately one hour. Following incubation, each mixture was filtered through a 100 kD MWCO membrane using a Millipore Minitan transverse flow filtration apparatus as shown in FIG. 2.

After filtration and concentration of the DOC-treated MBP sample, the retentate and filtrate were brought up to their original volumes so that the concentrations of HA and endotoxin could be directly compared.

Haemagglutinin concentrations in the filtrate and retentate were determined by means of an Enzyme-Linked Immunosorbant Assay (ELISA) and by radial immunodiffusion. Endotoxin levels were determined using an automated LAL assay (Bio Whittaker Colorimetric Kinetic K-QCL LAL Assay). Electron micrographs of the test sample before and after treatment with DOC were taken using a Phillips 300 Transmission Electron Microscope to determine the effect of the DOC on the rosette clusters of influenza surface antigens. The results of the HA ELISA and SRD assays are summarised in Tables 1 and 2 below.

Small Scale Results

TABLE 1

Summary of results showing the effect of DOC treatment (5 mM and 50 mM) on % HA in Retentate and Filtrate (0 mM DOC was used as a control).

| Expt No. | Test Vol. (L) | Conc of DOC (Mm) | Conc[b] Factor | HA: percentage of original | | | |
|---|---|---|---|---|---|---|---|
| | | | | ELISA | | SRD | |
| | | | | Retentate | Filtrate | Retentate | Filtrate |
| A/Texas Batch 531 | | | | | | | |
| 1 | 1.0 | 0 (control) | 10 | 49.2 | 1.5 | ND[c] | ND[c] |
|   | 1.0 | 50[a] | 10 | 57.6 | 5.3 | ND[c] | ND[c] |
| 2 | 1.0 | 0 (control) | 10 | 80.9 | 0.7 | ND[c] | ND[c] |
|   | 1.0 | 50 | 10 | 84.7 | 1.6 | ND[c] | ND[c] |
| 3 | 0.26 | 0 (control) | 5 | 41.9 | 0.8 | ND[c] | ND[c] |
|   | 0.26 | 5 | 5 | 137.2 | 3.1 | ND[c] | ND[c] |
| A/Texas Batch 570 | | | | | | | |
| 4 | 0.5 | 0 (control) | 7.1 | 50.4 | 13.2 | 64.5 | 18.2 |
|   | 0.5 | 5 | 10 | 95.7 | 4.0 | 107.6 | 11.4 |
| B/Panama Batch 387 | | | | | | | |
| 5 | 0.4 | 0 (control) | 8.3 | 75.6 | 0.0 | ND[c] | ND[c] |
|   | 1.0 | 5 | 2.7 | 74.9 | 0.3 | ND[c] | ND[c] |

[a]50 mM DOC start sample not taken therefore 0 mM DOC start sample used as divisor to calculate % HA and % LPS in 50 mM DOC retentate and filtrate samples.
[b]The concentration factor denotes the concentration of the antigen in the solution following the filtration and concentration steps, relative to the concentration of antigen after dilution.
[c]ND = Not done.

The HA and LPS levels (%) were calculated as follows:

$$\frac{\text{level in retentate or filtrate for } x \text{ mM } DOC}{\text{level in start } MPB \text{ for } x \text{ mM } DOC} \times 100$$

TABLE 2

Comparison of actual MBP HA levels pre and post diafiltration with and without 0.2% (5 mM) DOC as measured by SRD

| A/Texas batch 570 | HA concentration (μg/ml) in Monoblend | |
|---|---|---|
| | Pre-filtration | Post-filtration |
| 0 mM DOC | 190 | 123 |
| 5 mM DOC | 68 | 69 |

The results of the HA assays show that generally HA does not pass through the membrane to any great extent in the presence of DOC. In one experiment (Experiment 4), the levels of HA in the filtrate for the test solution (5 mM DOC) were rather higher than in the other experiments. This may be due to the particular batch of HA containing a larger percentage of HA in monomer form, the molecular weight (77 kD) of which would allow it to pass through the 100 kD MWCO membrane.

Determination of Endotoxin Levels

The endotoxin levels were assayed before and after treatment with DOC and diafiltration and dialysis as described above and the results are shown in FIGS. 3 and 4.

Figure 3:
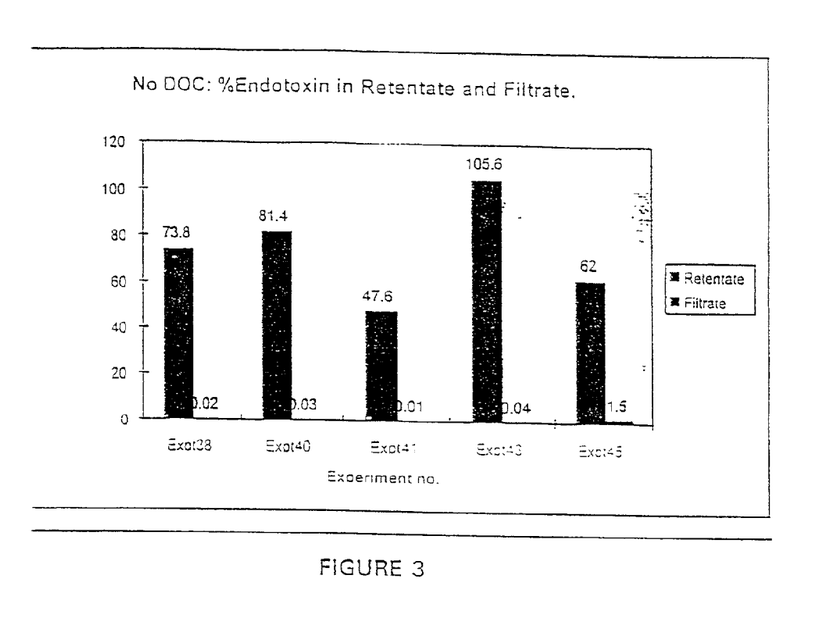
FIG. 3 is a bar graph showing the amount (by percentage) of endotoxin retained in the antigen solution in the absence of treatment with a surfactant.
Figure 4:
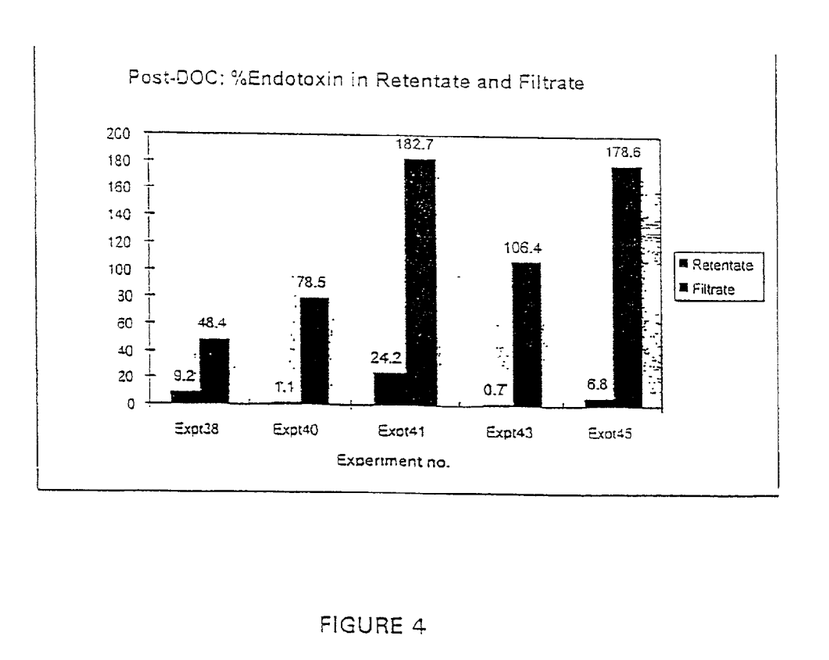
FIG. 4 is a bar chart illustrating the effect of sodium deoxycholate on the amount (by percentage) of endotoxin remaining in the antigen solution after filtration through a MWCO membrane.

The results illustrated in FIG. 3 show that diafiltration alone will not remove endotoxin from the MBP. When DOC is added (FIG. 4) and the solution is filtered, the levels of endotoxin in the retentate (bulk product) are substantially reduced compared to the pre-treatment levels. The levels of endotoxin in the filtrate (waste) increased correspondingly. Both concentrations of DOC (5 mM and 50 mM) were effective in removing endotoxin from MBP.

EXAMPLE 2

Pilot Scale Experiment

The small scale experiments described in Example 1 were scaled up by treating a batch of 4.32 L Influenza A/Texas Batch #531 MBP with 2% w/v disodium phosphate to give a pH of 8.15, adding 0.2% w/v DOC and then filtering through a 100 kD MWCO Low Binding regenerated cellulose acetate membrane (Millipore). As a control, influenza A/Texas Batch #531 MBP was filtered through the same membrane but without having been treated with DOC. After diafiltration and prior to measurement of the endotoxin levels, each of the solutions was made up to the volume (4.3 L) of the starting solution.

FIG. 5 illustrates the resulting distribution of the endotoxin in the starting solutions, retentates and filtrates. The results shown in FIG. 5 illustrate that as with the small scale experiments, greater than 90% of the endotoxin can be removed by diafiltration in the presence of deoxycholate.

The haemagglutinin concentrations were determined by ELISA and SRD as described above in Example 1.

The HA level pre- and post-DOC treatment of 4.32 L of endotoxin contaminated MBP were found to be substantially identical, within the limits of experimental error. Thus the HA level prior to treatment with DOC was 68.25 μg/ml and the level of HA detected after DOC treatment was 68.75 μg/ml. These results indicate that DOC treatment has not affected the HA epitopes.

EXAMPLE 3

Size Exclusion Chromatography (SEC) Using HPLC

An endotoxin contaminated monoblend pool (MBP) was passed down an SEC column (G43000 SWXL) eluting with 10 mM PBS at pH8 with and without 50 mM DOC to determine (a) whether DOC has any effect on the size of HA rosettes and (b) whether HA and endotoxin elute in the same fraction thereby indicating that they may be associated.

Thus, A/Texas #531 MBP concentrated ten-fold was examined by SEC with 0% and 0.2% (50 mM) DOC to determine whether the presence of DOC affects the molecular radius of HA and to establish whether the HA exists as a separate molecule in more aggregated forms. The fractions obtained were analysed for HA and endotoxin and were compared with the 280 nm protein absorbance elution profile (see FIGS. 6 and 7). DOC was found not to absorb light between 800 and 200 nm so the absorbance patterns for A/Texas MBP with 0 and 50 mM DOC could be directly compared. The results of the HA-ELISA show an HA peak coinciding with the 280 nm protein peak at around 3000 kD in the presence of both 0% and 0.2% DOC. These results, which demonstrate that the HA rosettes elute in the same position with or without DOC, indicate that the HA molecules adopt an aggregated rosette form which is not disrupted by 50 mM DOC treatment.

Figure 6:
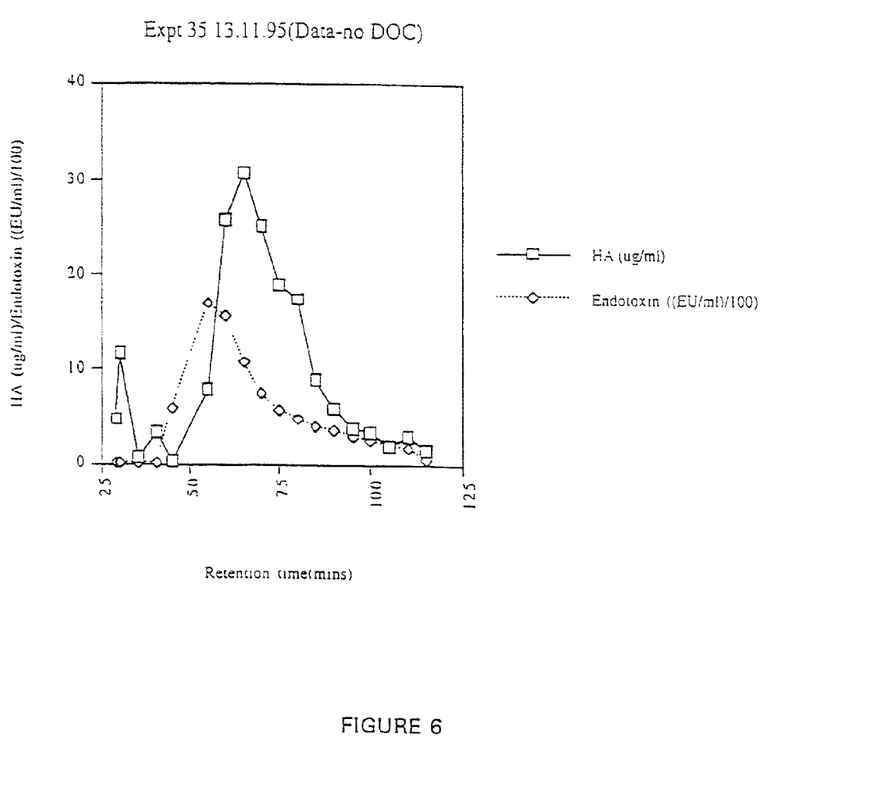
FIGS. 6 and 7 illustrate HA, and endotoxin and $A_{280}$ measurements of fractions collected from size exclusion chromatography (SEC) analyses of antigen preparations treated with 0% and 2% w/v (50 mM) DOC respectively.

Endotoxin co-elutes with HA when DOC is not present showing that the endotoxin is probably associated with the HA rosettes (FIG. 6).

Figure 7:
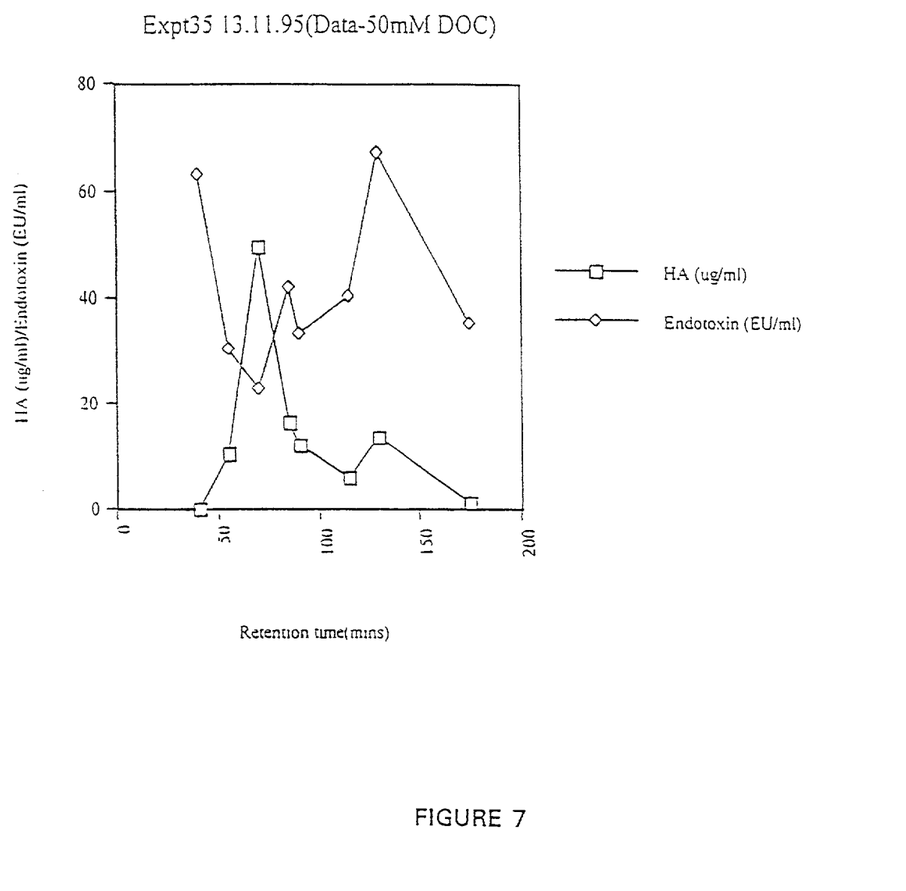

No conclusions can be drawn from the SEC fraction endotoxin profile of the sample containing 50 mM DOC as the endotoxin measurement in the LAL test is inhibited by the presence of DOC (FIG. 7).

In FIG. 7, the second peak appearing at 90 minutes may be explained by light diffraction by detergent micelles. Such micelles may contain a low level of protein (of the 280 nm profile) and may contain endotoxin.

Figure 8A:
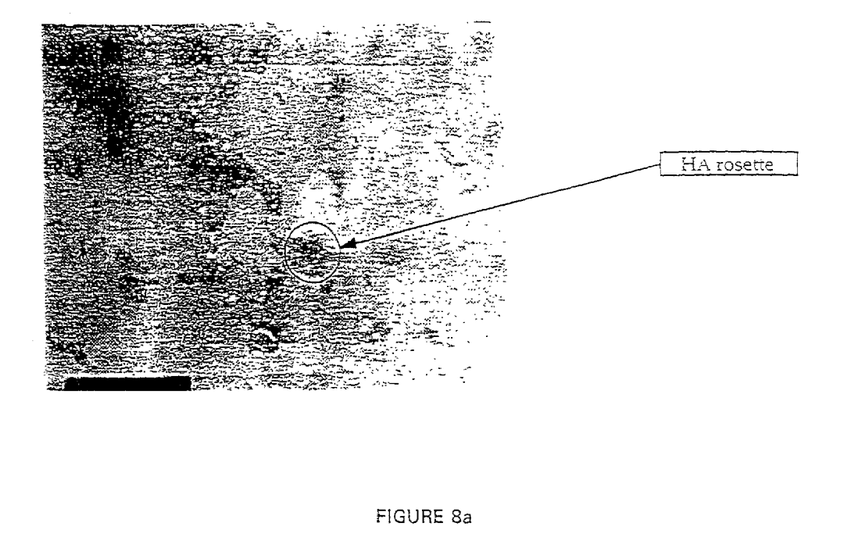
FIGS. 8a and 8b show electron micrographs of an influenza A/Texas #531 monoblend pool (MBP) before and after treatment with 2% w/v (50 mM) sodium deoxycholate (DOC) followed by diafiltration through a 100 kD MWCO membrane and then dialysis against PBS using a 10 kD MWCO membrane to remove DOC.
Figure 8B:
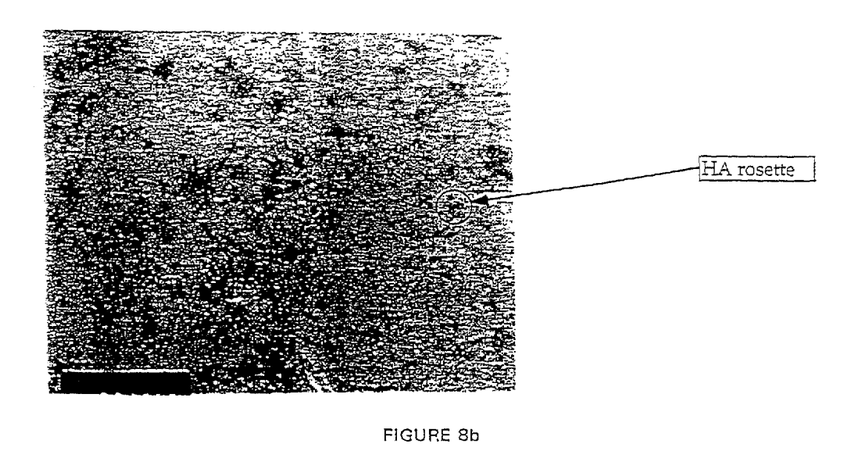

EM photographs show HA rosettes of mean diameter of about 34 nm pre and post-DOC treatment which also indicate that the HA rosettes are not disrupted by 2% DOC (see FIGS. 8a and 8b).

Figure 5:
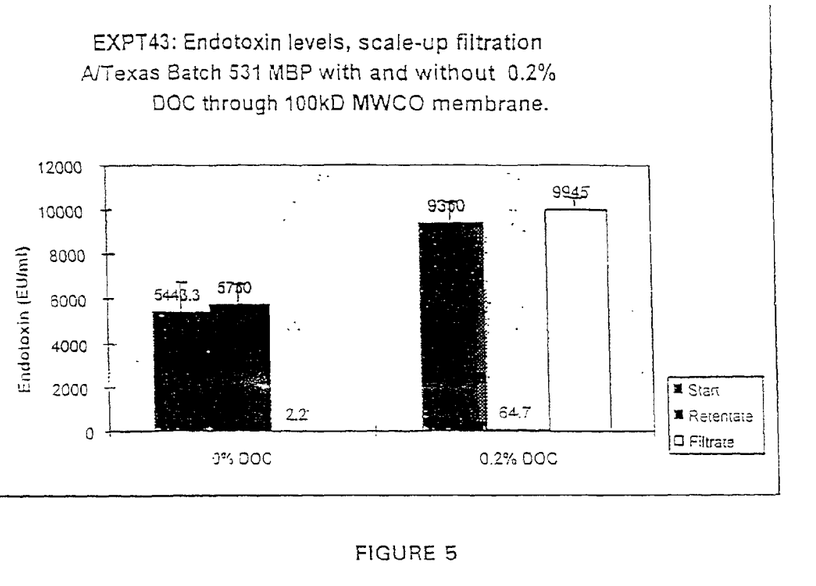
FIG. 5 illustrates the endotoxin levels in a pilot scale batch of influenza A/Texas #531 with and without pretreatment with 0.2% (w/v) sodium deoxycholate (DOC) before and after filtration through a 100 kD MWCO membrane.

The results presented in the above Examples illustrate that when MBP is diafiltered in the absence of DOC, endotoxin does not cross the 100 kD MWCO membrane, and remains in the retentate with the HA rosettes (FIG. 5). Analysis of size exclusion chromatography fractions (FIG. 6) with 0% DOC demonstrated the elution of endotoxin to be concurrent with HA, indicating they may be physically associated. Addition of 5 to 50 mM DOC allows endotoxin to cross the 100 kD MWCO membrane freely into the filtrate and therefore be separated from HA (FIGS. 3, 4 and 5 and Table 1) which does not cross the MWCO membrane to any great extent. Without wishing to be bound by any theory, it is considered that the affinity of DOC for the endotoxin could be greater than the affinity of endotoxin for the HA rosette such that the endotoxin binds to DOC rather than HA. It is possible that endotoxin molecules cross the 100 kD MWCO membrane in the form of mixed endotoxin/DOC micelles. Such micelles would need to have molecular weights less than 100 kD in order to pass through the filter membrane.

The results obtained illustrate that MBP HA derived from A/Texas #531, A/Texas #570 and B/Panama #87 does not cross the 100 kD MWCO membrane with 5 mM or 50 mM DOC to any significant extent since virtually no HA is measured in the filtrate by HA-ELISA (see Table 1). This indicates that the HA rosette or protein trimer do not dissociate into molecules smaller than 100 kD. The molecular weight of individual HA trimers is estimated to be 230 kD and so theoretically they should not pass through the 100 kD MWCO membrane. HA trimers do not appear to be reduced to 77 kD constituent monomers in the presence of DOC.

Removal of DOC is an important step because (a) it is not desirable in the end product and (b) separation of endotoxin from the contaminated MBP cannot be measured if DOC is present in samples. In one experiment DOC was successfully removed to less than 0.002% from retentate samples originally containing around 0.5% DOC by diafiltration across a 30 kD MWCO.

Thus the foregoing results demonstrate that sodium deoxycholate treatment of antigen solutions followed by filtration through a molecular weight cut-off filter membrane can provide an efficient means of separating endotoxin from vaccine preparations, despite previous preconceptions that this could not be achieved on a large scale.

The foregoing examples illustrate the invention but are not intended to be in any way limiting as to the scope of the invention. For example it is envisaged that other detergents having similar properties to DOC may be useful in the process of the invention, and it is envisaged that the method will find use in the removal of endotoxin from antigens other than influenza antigens and also from other pharmaceutical drug products (e.g. other polypeptides) in which endotoxin contamination is a potential problem.

The invention claimed is:

1. A method of removing bacterial endotoxin from a pharmaceutical process solution containing an amphiphilic pharmaceutical drug or vaccine, wherein said method comprises:
   a) treating the pharmaceutical process solution with a concentration of sodium deoxycholate that is effective to dissociate the endotoxin from the amphiphilic pharmaceutical drug or vaccine in the pharmaceutical process solution without affecting the ability of the drug or vaccine to be retained by a molecular cut-off filter having a pore size effective to retain the amphiphilic pharmaceutical drug or vaccine substance but allow the disassociated bacterial endotoxin to pass through;
   b) directly thereafter filtering the treated pharmaceutical process solution though a 30 kDa molecular weight cut-off filter; and
   c) thereafter, subjecting the filtered pharmaceutical process solution to a further process step in which the sodium deoxycholate is removed, wherein after this process step the amount of sodium deoxycholate remaining in the pharmaceutical process solution is less than 0.002%.

2. The method according to claim 1, wherein the amphiphilic pharmaceutical drug or vaccine comprises a polypeptide.

3. The method according to claim 2, wherein the amphiphilic pharmaceutical drug or vaccine comprises a glycoprotein.

4. The method according to claim 1, wherein the amphiphilic pharmaceutical drug or vaccine is an antigen.

5. The method according to claim 4, wherein the antigen is a viral antigen.

6. The method according to claim 5, wherein the antigen is an influenza antigen.

7. The method according to claim 5, wherein the antigen is a haemagglutinin and/or neuramidase antigen.

8. The method according to claim 1, wherein the concentration of the sodium deoxycholate added in step a) is at least as great as its critical micelle concentration.

9. The method according to claim 8, wherein the concentration of the sodium deoxycholate added in step a) is from one and a half to five times its critical micelle concentration.

10. The method according to claim 8, wherein the concentration of the sodium deoxycholate added in step a) is from two to four times its critical micelle concentration.

11. The method according to claim 1, wherein the molecular weight cut-off filter comprises a regenerated cellulose acetate membrane, or a polysulfone membrane.

12. The method according to claim 1, wherein the further process step comprises subjecting the filtered pharmaceutical process solution to dialysis.

* * * * *